United States Patent [19]

Merz et al.

[11] 4,058,526

[45] Nov. 15, 1977

[54] TREATMENT OF WASTE WATER FROM THE PREPARATION OF 6-SUBSTITUTED 3-MERCAPTO-4-AMINO-1,2,4-TRIAZINE-5-ONES

[75] Inventors: Walter Merz, Leverkusen; Günter Schümmer, Cologne, both of Germany

[73] Assignee: Bayer Aktiengesellschaft, Leverkusen, Germany

[21] Appl. No.: 685,234

[22] Filed: May 11, 1976

[51] Int. Cl.$^2$ .......................................... C07D 253/06
[52] U.S. Cl. ...................................... 544/182; 210/21
[58] Field of Search ..................... 260/248 AS; 210/21

[56] References Cited

U.S. PATENT DOCUMENTS 3,905,801  9/1975  Fawzi ........................... 260/248 AS Primary Examiner—John M. Ford
Attorney, Agent, or Firm—Burgess, Dinklage & Sprung

[57] ABSTRACT

A process for the treatment of waste water obtained in the condensation of thiocarbohydrazide and an aqueous solution of an α-keto carboxylic acid such as, e.g., 3,3-dimethyl-2-oxo-butyric acid, which comprises mixing said waste water with a water-immiscible ketone, preferably selected from the group consisting of methyl isobutyl ketone, cyclohexanone and pinacolone, said ketone being employed in an amount sufficient to form two phases, separating said two phases, and discharging as waste the aqueous phase. Advantageously the pH of the waste water is no higher than about 6 and its temperature is 20° to 50° C. The organic phase comprises the ketone containing dissolved therein an adduct of the ketone with thiocarbohydrazide and/or similar amino materials originally present in waste water. The excess of the ketone may be recovered from the organic phase by distillation, or the organic phase may be treated with alkali to effect hydrolysis of such adducts, the ketone separated and recycled and the amino materials recovered.

12 Claims, 1 Drawing Figure

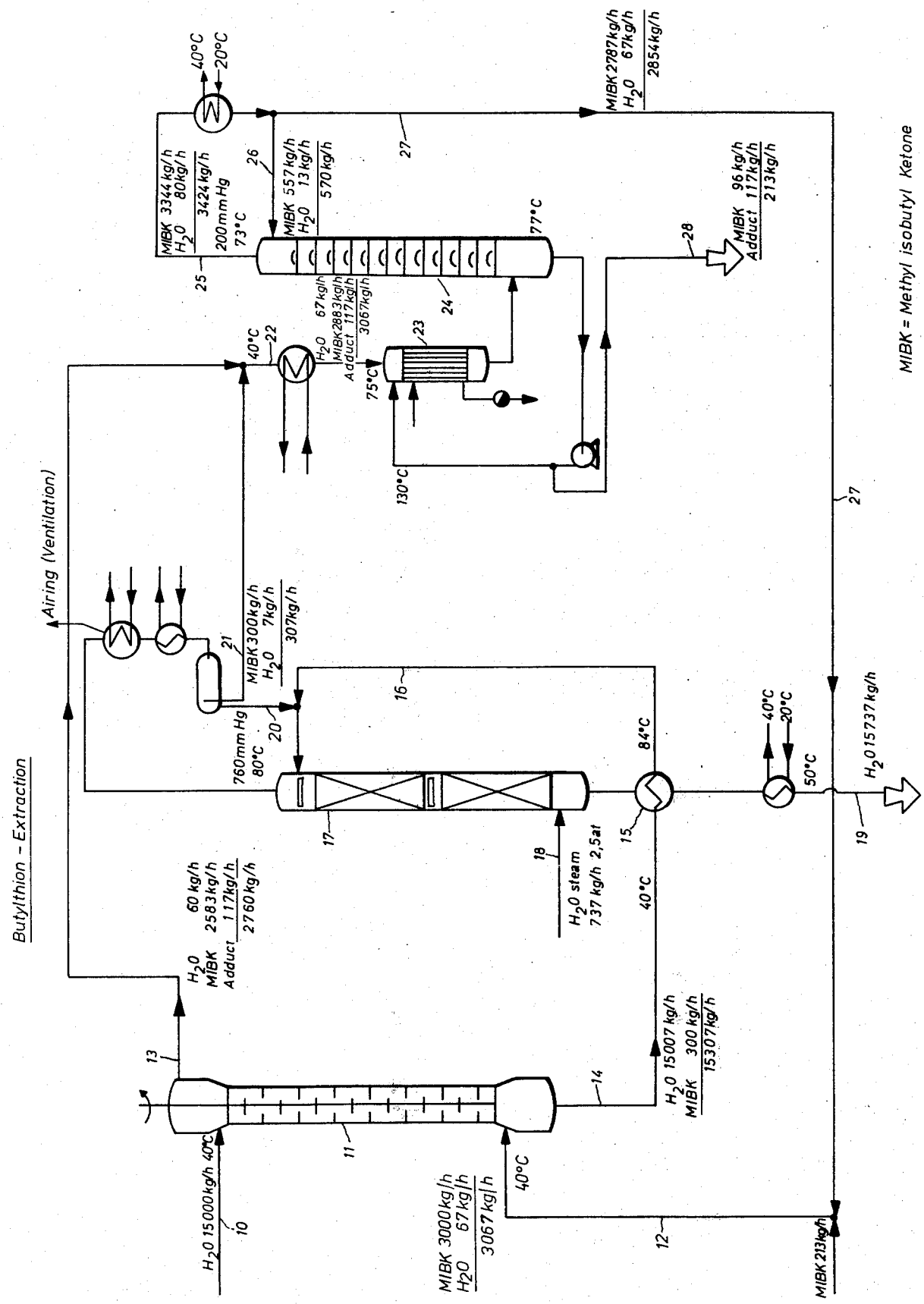

TREATMENT OF WASTE WATER FROM THE PREPARATION OF 6-SUBSTITUTED 3-MERCAPTO-4-AMINO-1,2,4-TRIAZINE-5-ONES

The present invention relates to a process for the treatment of waste water from the condensation of thiocarbohydrazide with an aqueous solution of α-keto carboxylic acid of the formula $$R-CO-COOH \quad (I)$$

in which
R is optionally substituted alkyl, optionally substituted cycloalkyl, optionally substituted aralkyl, optionally substituted aryl or an optionally substituted heterocyclic radical to produce 6-R-substituted 3-mercapto-4-amino-1,2,4-triazin-5-ones or their 3-thione tautomers, viz.

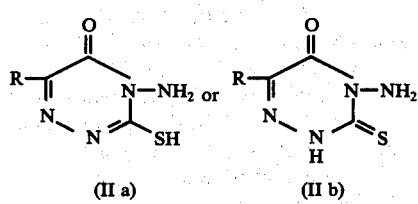

in which
R has the same meaning as stated above.

R in formulae (I) and (II) is preferably alkyl of from 1 to 18 carbon atoms, cycloalkyl of from 5 to 6 carbon atoms, aralkyl of from 6 to 10 carbon atoms in the corresponding aryl moiety and 1 to 4 carbon atoms in the alkylene moiety, aryl of from 6 to 10 carbon atoms or a heterocyclic radical having 5 to 6 ring members with at least one hetero linking atom selected from the group consisting of O, N, S and mixtures of such hetero atoms, and such alkyl, cycloalkyl, aralkyl, aryl and heterocyclic radical, respectively, which is substituted with at least one substituent selected from the group consisting of halo, nitro, carbo lower alkoxy, lower alkyl, lower alkoxy, aryloxy having 6–10 ring carbon atoms, lower alkylmercapto, arylmercapto having 6–10 ring carbon atoms, aryl-lower alkylmercapto having 6–10 ring carbon atoms in the aryl moiety, and mixtures of such substituents.

In accordance with a more preferred embodiment of this invention, R is alkyl of from 1 to 4 carbon atoms, especially tert.-butyl.

In particular, Application Ser. No. 640,830, filed Dec. 15, 1975, now pending, discloses the condensation of thiocarbohydrazide with an aqueous solution of 3,3-dimethyl-2-oxo-butyric acid ("trimethyl pyruvic acid") to produce 3-mercapto-4-amino-6-tert.-butyl-1,2,4-triazine-5-one or its 3-thione tautomer ("butylthion") of the formula

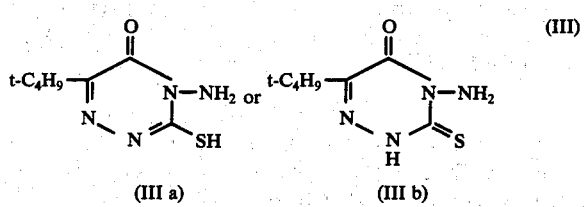

which, upon S-methylation with methyl iodide or bromide, produces the exceptionally effective selective herbicide 3-methylmercapto-4-amino-6-tert.-butyl-1,2,4-triazin-5-one ("metribuzin") (U.S. Pat. No. 3,671,523).

In putting this process into practice it has been found that there is a waste disposal problem in that the waste water contains organic materials which do not permit its direct discharge into streams, i.e., it will consume dissolved oxygen and would therefore be damaging to fish and the like. In addition, there would take place an undesirable anaerobic fermentation of the discharged materials in the streams as soon as all dissolved oxygen has been consumed.

In the following, there are used the terms "COD" and "BOD$_5$," which mean "chemical oxygen demand" and "biochemical oxygen demand within 5 days", respectively, to determine the degree of contamination of the waste water with organic material (see textbook "Standard Methods for the Examination of Water and Waste Water", American Public Health Association, 1015, Eighteenth St., N.W. Washington, D.C. 20036, 1971).

Specifically, analysis reveals that said waste water has a COD value of about 20,000 to 50,000 mg of O$_2$ per liter and a BOD$_5$ value of about 1,500 to 2,500 mg of O$_2$ per liter. In addition to some thiocarbohydrazide, the dissolved organic compounds include pivalic acid, trimethyl pyruvic acid and thiocarbohydrazide-like materials.

Extraction with a variety of solvents having a variety of functional groups has proven ineffective, e.g., petroleum ether, ethylene chloride, toluene, diisopropyl ether and ethyl acetate, so there is still a serious problem of waste disposal.

It is accordingly an object of the invention to provide a process for treating such waste water to permit its direct discharge. It is another object of the invention to provide such a process which also permits recovery of the organic values in such waste water.

It has now been found that a small group of solvents is especially suited for the purpose, viz. water-immiscible ketones, such as methyl isobutyl ketone, cyclohexanone and pinacolone. These have a special combination of properties which render them useful. They are of very limited water solubility so they are suited for two phase liquid extraction. They are reactive and form adducts with excess thiocarbohydrazide contained in the waste water as well as with some dissolved butylthion contained therein and other reactive compounds. These adducts are selectively soluble in the particular ketones as opposed to water. Finally, the adducts can be decomposed to their components so the ketone can be recycled and the other components can be isolated and/or recycled.

The ketone is mixed with the waste water in any amount in excess of that required to form two liquid phases, i.e., to react to form the adducts and to dissolve to its maximum limit in the water layer; unnecessarily large excesses, though obviously wasteful, are still operative.

The adduct with methyl isobutyl ketone, for example, is believed to form as follows:

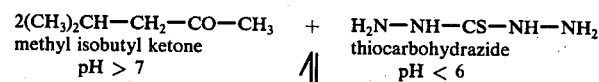
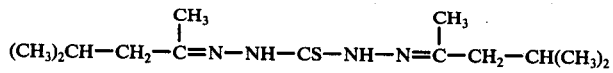

The temperature of extraction should not be too high since the solubility of the ketones in water will be too high and result in loss. If too low, the adducts will not be sufficiently soluble. A temperature of about 20° to 50° C is quite satisfactory.

The pH of the waste water is adjusted to about 6 or less (advantageously 1-3) by addition of any acid. This apparently favors the existence of the aforementioned adduct which exists in equilibrium with the free compounds.

After mixing the liquids in conventional manner, settling and separation, the aqueous water phase can be discharged, after stripping to remove any ketone dissolved in such aqueous phase, since it is extremely low in organic content (its COD value being about 2,000 to 10,000 mg of $O_2$ per liter), or it may be re-extracted prior to discharge. Alternatively, part of it may be recycled to earlier synthesis steps. The organic phase can be subjected to distillation to separate the volatile ketone from the non-volatile adduct, the ketone being recycled and the adduct processed to effect decomposition of the adduct by shifting the equilibrium and thereby form more ketone, all of which can be separated in a single distillation procedure. Decomposition also liberates the amino components which can be isolated and recovered or recycled to the process for preparing 6-subst. 3-mercapto-4-amino-1,2,4-triazin-5-ones such as butylthion. The distillation residues can be recovered or burned.

The invention will be further described with reference to the accompanying drawing which is a flow sheet of an apparatus for carrying out the present invention.

Referring now more particularly to the drawing, waste water is introduced at 10 to the top of a multiplate extractor column 11 and ketone is introduced at 12 to enter at the bottom of the column. The column overflow is withdrawn at 13, comprising ketone having organics dissolved therein, while the underflow at 14 comprises waste water with a small amount of dissolved ketone. The waste stream is heated in a heat exchanger 15 and is supplied at 16 near the top of a stripper column 17 which is directly supplied with stream at 18. The aqueous underflow from column 17, at 19, can be directly discharged, being largely freed of its initial organic content. Alternatively, it can be conducted into a settling tank (not shown) after cooling, and later be discharged.

The ketone stripped in column 17 is partially refluxed at 20 and the balance is combined with overflow 13 through line 21, the merged stream 22 preheated in a heat exchanger 23 and introduced near the bottom of a distillation column 24. Distilled ketone comes off at 25, condenses, is partially refluxed at 26 and mostly recycled through line 27 to extractor column 11. The relatively high melting residue is withdrawn at 28.

The values for amounts of material and the temperatures shown on the drawing are those in connection with Example 1 hereinbelow.

The invention will be further described in the following illustrative examples wherein all parts are by weight unless otherwise expressed.

EXAMPLE 1

Employing an apparatus as shown in the drawing wherein column 11 has 15 plates, a diameter of 1.2 m and a height of 3.75 m, 15,000 Kg/hour of butylthion waste water having a COD value of about 40,000 mg of $O_2$ per liter and a $BOD_5$ value of about 2,000 mg of $O_2$ per liter, are introduced at 10 and 3000 kg/hour of methyl isobutyl ketone are introduced at 12. The aqueous phase contains 300 Kg/hour of dissolved methyl isobutyl ketone which is distilled off by direct application of steam to stripper 17 which is 3.0 m high and 0.6 m in diameter. The stripped waste water, having a COD value of about 3,000 mg of $O_2$ per liter and a $BOD_5$ value of about 500 mg of $O_2$ per liter, is permitted to cool and passed to a settling tank for ultimate discharge to waste (at 19).

The organic phase is freed of most of the methyl isobutyl ketone (2787 Kg/hour) by continuous distillation in 12-plate column 24 (1.1 m diameter × 3.6 m high) under 200 mm Hg absolute, the head temperature being 73° C and the sump temperature being 77° C. 213 Kg/hour of sump residue are obtained, comprising 96 Kg/hour of methyl isobutyl ketone and 117 Kg/hour of adduct (at 28).

EXAMPLE 2 a. 2 Liters of the butylthion waste water are extracted with 400 ml of methyl isobutyl ketone. After phase separation and removal of the aqueous layer, the organic layer is azeotropically distilled with 50 ml of added water and 0.5 g of caustic soda. The condensate is collected, stratified and the water recycled to the distillation. The methyl isobutyl ketone distillate is recovered for re-use. The distillation residue is 85 g of a mixture of 20 g of water which can be re-cycled and 65 g of a solidified smeary mass comprising about 45% of water and which can easily be burned.

b. If the process of (a) is carried out in the equipment and on the scale of Example 1, i.e. introduction of alkali into column 24, the waste at line 28 constitutes only 70 Kg/hour of ultimate solids of which about 45% is water. 2967 Kg/hour (=180 Kg/hour in addition to 2787 Kg/hour as shown in Example 1) of methyl isobutyl ketone is recovered in the distillation being recycled through line 27.

EXAMPLE 3

1 liter of a butylthion waste water having a COD value of 22,220 mg of $O_2$ per liter and containing 5,350 mg of carbon (i.e. organically bonded carbon) per liter is shaken with 200 ml of ketone, the aqueous phase separated and similarly re-extracted 3 more times. After the fourth extraction the aqueous phase is stripped of solvent and analyzed. The results with different ketones are as follows:

| a) | methyl isobutyl ketone | |
|---|---|---|
| | COD | 5,920 mg of $O_2$ per liter |
| | carbon (organically bonded) | 645 mg of C per liter |
| b) | cyclohexanone | |
| | COD | 8,500 mg of $O_2$ per liter |
| | carbon (organically bonded) | 1,725 mg of C per liter |
| c) | pinacolone | |
| | COD | 6,960 mg of $O_2$ per liter |
| | carbon (organically bonded) | 840 mg of C per liter |

EXAMPLE 4

43 Liters of the same butylthion waste water as in Example 3 are twice extracted with 2.1 liters of ethylene chloride each time. The two organic extracts are evaporated, leaving only 51 g of a residue containing approximately 36 g of pivalic acid.

For comparison, the already extracted aqueous phase is thereafter twice extracted with 2.1 liters of methyl isobutyl ketone. Evaporation of both extracts leaves 435 g of a solid residue, m.p. 80°-100° C. The aqueous phase, after stripping, has a COD value of 2,300 mg of $O_2$ per liter.

It will be understood that the specification and examples are illustrative but not limitative of the present invention and that other embodiments within the spirit and scope of the invention will suggest themselves to those skilled in the art.

What is claimed is:

1. In the condensation of thiocarbohydrazide and an aqueous solution of an α-keto carboxylic acid of the formula $$R—CO—COOH \qquad (I)$$

in which

R is alkyl of from 1 to 18 carbon atoms, cycloalkyl of from 5 to 6 carbon atoms, aralkyl of from 6 to 10 carbon atoms in the aryl moiety and 1 to 4 carbon atoms in the alkyl moiety, or aryl of from 6 to 10 carbon atoms and such alkyl, cycloalkyl, aralkyl and aryl radical, respectively, which is substituted with at least one substituent selected from the group consisting of halo, nitro, carbo lower alkoxy, lower alkyl, lower alkoxy, aryloxy having 6–10 ring carbon atoms, lower alkylmercapto, arylmercapto having 6–10 ring carbon atoms and aryl lower alkylmercapto having 6–10 ring carbon atoms in the aryl moiety, to produce a triazinone of the formula

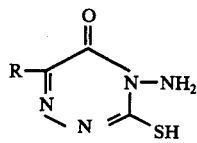

and waste water, and separating the triazinone from the waste water, the improvement which comrpises treating said waste water, said treatment involving mixing said waste water with a water-immiscible ketone solvent, said ketone being employed in an amount sufficient to form an aqueous phase and a ketone phase, and separating the thus purified waste water aqueous phase from the ketone phase.

2. A process as claimed in claim 1, wherein R of formula (I) is alkyl of from 1 to 4 carbon atoms.

3. A process as claimed in claim 1, wherein R of formula (I) is tert.-butyl.

4. A process as claimed in claim 1, wherein the ketone is selected from the group consisting of methyl isobutyl ketone, cyclohexanone and pinacolone.

5. A process as claimed in claim 1, wherein the pH of the aqueous solution mixed with the ketone is no higher than about 6.

6. A process as claimed in claim 1, wherein the pH of the aqueous solution mixed with the ketone is about 3 to 4.

7. A process as claimed in claim 1, wherein the ketone is separated from the organic phase and is recycled.

8. A process as claimed in claim 6, wherein the organic phase is treated with alkali to raise its pH above 7 to effect hydrolysis of material contained therein prior to separation of the ketone therefrom.

9. A process as claimed in claim 1, wherein the ketone is methyl isobutyl ketone.

10. A process as claimed in claim 1, wherein the ketone is cyclohexanone.

11. A process as claimed in claim 1, wherein the ketone is pinacolone.

12. A process as claimed in claim 7, wherein the ketone is methyl isobutyl ketone, and the waste water is stripped to remove methyl isobutyl ketone which is also recycled.

* * * * *